United States Patent
Reichwein et al.

(10) Patent No.: US 10,472,320 B2
(45) Date of Patent: *Nov. 12, 2019

(54) PROCESS TO PREPARE PHENOLIC ETHYLENEDIAMINE DIACETIC ACID COMPOUNDS

(71) Applicant: Akzo Nobel Chemicals International B.V., Arnhem (NL)

(72) Inventors: Adrianus Maria Reichwein, Velp (NL); Hubertus Johannes Jongen, Gendringen (NL); Marjolein Groote, Deventer (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 22 days.

This patent is subject to a terminal disclaimer.

(21) Appl. No.: 15/736,372

(22) PCT Filed: Jun. 23, 2016

(86) PCT No.: PCT/EP2016/064501
§ 371 (c)(1),
(2) Date: Dec. 14, 2017

(87) PCT Pub. No.: WO2016/207266
PCT Pub. Date: Dec. 29, 2016

(65) Prior Publication Data
US 2018/0186727 A1    Jul. 5, 2018

(30) Foreign Application Priority Data
Jun. 25, 2015    (EP) .................................. 15173800

(51) Int. Cl.
*C07C 227/18* (2006.01)
*C07C 227/16* (2006.01)

(52) U.S. Cl.
CPC .......... *C07C 227/18* (2013.01); *C07C 227/16* (2013.01)

(58) Field of Classification Search
CPC ........................... C07C 227/16; C07C 227/18
See application file for complete search history.

(56) References Cited

U.S. PATENT DOCUMENTS

| | | | |
|---|---|---|---|
| 2,967,196 | A | 1/1961 | Kroll et al. |
| 3,632,637 | A | 1/1972 | Martell |
| 4,338,460 | A | 7/1982 | Gaudette et al. |
| 4,482,626 | A | 11/1984 | Twist et al. |
| 5,342,604 | A | 8/1994 | Wilson et al. |
| 5,776,894 | A | 7/1998 | Albert et al. |
| 6,242,492 | B1 | 6/2001 | Bergeron, Jr. |
| 8,629,293 | B2 | 1/2014 | Olszewski et al. |
| 10,093,612 | B2 * | 10/2018 | Reichwein ............ C07C 227/18 |
| 2001/0039295 | A1 | 11/2001 | Bergeron, Jr. |
| 2004/0115572 | A1 | 6/2004 | Tsukada et al. |
| 2004/0121273 | A1 | 6/2004 | Nakagawa et al. |
| 2006/0068341 | A1 | 3/2006 | Inoue |
| 2007/0099132 | A1 | 5/2007 | Nakagawa et al. |
| 2007/0202276 | A1 | 8/2007 | Arai et al. |
| 2007/0202277 | A1 | 8/2007 | Arai et al. |
| 2007/0203024 | A1 | 8/2007 | Takehara et al. |
| 2008/0241732 | A1 | 10/2008 | Hosokawa et al. |
| 2008/0248951 | A1 | 10/2008 | Yoshitani et al. |
| 2010/0168469 | A1 | 7/2010 | Nawrocki et al. |
| 2014/0292940 | A1 | 10/2014 | Cordwell et al. |

FOREIGN PATENT DOCUMENTS

| | | |
|---|---|---|
| WO | 01/46114 A1 | 6/2001 |
| WO | 2016/207265 A1 | 12/2016 |

OTHER PUBLICATIONS

Kean et al., "Iron chelating agents and their effects on the growth of *Pseudokirchneriella subcapitata, Chlorella vulgaris, Phaeodactylum tricornutum* and *Spirulina platensis* in comparison to Fe-EDTA," Journal of Algal Biomass Utilization, 2015, 6 (1), pp. 56-73, Retrieved from the Internet: URL:http://jalgalbiomass.com/paper7vo16no1.pdf retrieved on Oct. 16, 2015, XP055221657.

Martell et al. "Synthesis of N,N'-di(2-hydroxybenzyl)ethylenediamine-N,N'-diacetic acid (HBED) and derivatives," Canadian Journal of Chemistry, vol. 64, No. 3, Mar. 1, 1986, pp. 449-456, CA ISSN: 0008-4042, DOI: 10.1139/v86-070, XP055221199.

J.G. Wilson, "Phenolic Analogues of Amino Carboxylic Acid Ligands for 99mTc. II* Synthesis and Characterization of N,N'-Ethylenebis[N-(o-hydroxybenzyl)-glycines] (ehbg)," *Aust. J. Chem.*, 1988, 41, pp. 173-182.

Chaney, "Plants Can Utilize Iron From Fe—N,N'—DI-(2-Hydroxybenzoyl)-Ethylenediamine-N,N'-Diacetic Acid, a Ferric Chelate With 106 Greater Formation Constant Than Fe-EDDHA," Journal of Plant Nutrition, 11(6-11), (1988). p. 1033-1051.

(Continued)

*Primary Examiner* — Sudhakar Katakam
*Assistant Examiner* — Jennifer C Sawyer
(74) *Attorney, Agent, or Firm* — Norris McLaughlin, P.A.

(57) ABSTRACT

The present invention relates to a process to prepare N,N'-di(2-hydroxybenzyl) ethylenediamine-N,N'-diacetic acid and salts thereof (HBED) comprising a reaction between formaldehyde, ethylenediamine diacetic acid or a salt thereof (EDDA) and phenol, wherein the reaction mixture contains 0.2 to 1.1 molar equivalents of alkali metal ions on the basis of the molar amount of EDDA and the reaction mixture is processed by a step in which at least part of the organic compounds other than the formed HBED are removed from the reaction mixture, and optionally recycled, during which step at least 50% and up to and including 100% of the alkali metal ions in the reaction mixture are potassium ions, to products obtainable by such process and their use.

12 Claims, No Drawings

(56) References Cited

OTHER PUBLICATIONS

European Search Report issued in the counterpart European Application No. 15173800.2 dated Oct. 30, 2015.
Notification of Transmittal of the International Search Report and the Written Opinion of the International Searching Authority, or the Declaration from the International Bureau of WIPO for International Application No. PCT/EP2016/064501 dated Sep. 13, 2016.
Notification of Transmittal of the International Preliminary Report on Patentability for International Application No. PCT/EP2016/064501 dated May 24, 2017.

\* cited by examiner

PROCESS TO PREPARE PHENOLIC ETHYLENEDIAMINE DIACETIC ACID COMPOUNDS

This application is a national stage filing under 35 U.S.C. § 371 of PCT/EP2016/064501, filed Jun. 23, 2016, which claims priority to European Patent Application No. 15173800.2, filed Jun. 25, 2015, the contents of each of which are each incorporated herein by reference in their entirety.

The present invention relates to a process to prepare phenolic ethylenediamine diacetic acid compounds and to phenolic ethylenediamine diacetic acid compounds obtainable with the process.

Phenolic ethylenediamine diacetic acid compounds are known in the art. An example of a phenolic ethylenediamine diacetic acid compound is N,N'-di(2-hydroxybenzyl)ethylenediamine-N,N'-diacetic acid, often abbreviated as HBED, though more specifically this molecule is o,o-HBED. The isomers o,p- and p,p-HBED may also be formed in HBED production processes, though in significantly smaller amounts. Preparation methods for this molecule are described in several documents such as in WO 2009/037235 and U.S. Pat. No. 3,632,637.

The process of WO 2009/037235 involves a reductive amination of glyoxylic acid with a salan compound that is made by reacting ethylenediamine with salicylaldehyde to give HBED isolated as a dry HCl solid. This reaction requires quite a number of steps, however, many of them of considerable complexity, and a number attended with high costs. These steps are, among others, filtering off the hydrogenation catalyst, working with H2, which requires safety measures, working under increased pressure, and using an excess of glyoxylic acid and amine proton acceptor, both of which need to be recycled before the formed HBED can be isolated in a crystalline form. Moreover, to prepare the iron chelate of HBED the crystals need to be dissolved again before they can be contacted with iron cations and next be dried again in the iron chelated form. The alkali metal salts of HBED are obtained as an aqueous solution by titrating HBED in the acidic form with 3 molar equivalents of either NaOH or KOH, which gives HBED as the full sodium and potassium salts, respectively. WO '235 is silent about any advantages of choosing potassium as a counterion.

The process of U.S. Pat. No. 3,632,637 involves reacting ethylenediamine diacetic acid with o-acetoxybenzyl halogenide, such as bromide or chloride. Though in general the HBED is said to be obtainable as an acid, a sodium, potassium or ammonium salt, the document only discloses the provision of HBED as a solid in acidic form and as a sodium salt.

In J. G. Wilson, "phenolic analogues of aminocarboxylic acid ligands for $^{99m}$Tc. II* Synthesis and characterization of N,N'-ethylenebis[N-(o-hydroxybenzyl glycines)] ehbg", *Aust J Chem* 1988, 41, 173-182, it is described that the above process of U.S. Pat. No. 3,632,637 is undesirable as it is marred by the formation of resinous polymeric by-products, creating a search for new preparation processes. In this same document reference is made to U.S. Pat. No. 2,967,196 as giving further preparation methods for making phenolic ethylenediamine diacetic acids.

U.S. Pat. No. 2,967,196 discloses a reaction wherein formaldehyde is added to an alkaline solution of ethylenediamine diacetic acid in methanol to which a para-substituted phenol such as p-cresol, p-phenolsulfonic acid or p-hydroxybenzoic acid is added. This is disclosed to be done to avoid a reaction of ethylenediamine diacetic acid with an o-chloromethyl derivative, which is said to be the only way to ensure the hydroxyl group ending up ortho to the ethylenediamine part of the molecule. The reaction conditions in this document involve reflux conditions, i.e. relatively high temperatures, and the reaction is preferably performed at an alkaline pH of between 8 and 10, by adding high amounts of either sodium or potassium hydroxide as a base. U.S. '196 does not recommend any alkali metal in particular for its process.

It is also confirmed in the above publication of J. G. Wilson that the reaction disclosed in U.S. Pat. No. 2,967,196 is not successful for unsubstituted phenols for the same ortho, para-position reason as referred to in U.S. '196.

However, there is a need in the art to provide a simple process to make HBED and derivatives thereof wherein ethylenediamine diacetic acid can be reacted with formaldehyde and phenol, in which the product is formed in good yield and in high purity.

The present invention now provides a process to prepare N,N'-di(2-hydroxybenzyl) ethylenediamine-N,N'-diacetic acid and salts thereof (HBED) comprising a reaction between formaldehyde, ethylenediamine diacetic acid or a salt thereof (EDDA), and phenol, wherein the reaction mixture contains 0.2 to 1.1 molar equivalents of alkali metal ions on the basis of the molar amount of EDDA and the reaction mixture is subsequently processed by a step in which at least part of the organic compounds other than the formed HBED are removed from the reaction mixture and optionally recycled, during which step 50-100% of the alkali metal ions in the reaction mixture are potassium ions. Preferably, the reaction between formaldehyde, EDDA and phenol is performed at a pH of between 3 and 7 and a temperature below 60° C.

Working within the scope of the process of the present invention it has been found possible to make HBED with a good selectivity for the ortho (to hydroxyl) position and a high yield of product in a limited number of steps, using cheap materials, wherein the reaction steps are easy to control because no highly exothermic steps are involved, no high pressure needs to be applied and not too hazardous materials are used, wherein pH control is relatively straightforward, wherein the reaction mixture is also easy to handle throughout the reaction, as it is homogeneous, and wherein the obtained HBED with 50-100% potassium as a counter-cation proved surprisingly easy to purify from the other reaction products and side products in a processing step, for example using an extraction step.

The present invention also provides the alkali metal-containing HBED products (full or partial salts and complexes that contain alkali metal as a cation) obtainable by the present invention wherein more than 50% but less than 100% of the alkali metal ions is potassium. It was found that as they were obtained by a different process, these products are different in the sense that they have another isomers distribution, contain low amounts of by-products and are an alkali metal-functional salt of HBED or derivative thereof wherein more than 50% but less than 100% of the alkali metal ions are potassium, such as a predominantly potassium-functional complex of HBED, like FeK-HBED, CuK$_2$-HBED, ZnK$_2$-HBED, MnK$_2$-HBED, MnK-HBED, in either dissolved or dry form. Additionally, the products of the process of the invention were found easy to dry. It should be noted that WO 2009/037235, WO 01/46114 and the disclosure of M A Kean et al: "Iron chelating agents and their effects on the growth of *Pseudokirchneriella subcapitata, Chlorella vulgaris, Phaeodactylum tricornutum* and *Spirulina platensis* in comparison to Fe-EDTA", *Journal of*

*Algal Biomass Utilization*, 2015, 6 (1), 1 Jan. 2015, pages 56-73, disclose either potassium salts or metal-potassium complexes of HBED in which the only alkali metal is potassium. The compounds covered by the present invention contrary to those compounds contain a combination of potassium and at least one further alkali metal. The products of the present invention, though different from those disclosed in the above 3 documents, can equally be used in similar applications, such as water softening, pulp and paper production, bleaching, detergents. Most preferably, they are used in micronutrient formulations.

In the process of the present invention the three reactants can be added together using different orders of steps. As the phenol reactant is used as a liquid—and in many embodiments is used in an excess amount—it is possible to either make a premix of the EDDA and the phenol and next add this mixture to the formaldehyde or vice versa, or to make a premix of the phenol and formaldehyde and add this premix to the EDDA or vice versa, and then perform the reaction under the above pH, alkali metal load, and temperature conditions. Another even more preferred way of performing the process is first making an adduct of the EDDA and formaldehyde and next reacting this adduct with the phenol under the mentioned pH, alkali metal load, and temperature conditions. This latter embodiment has as an advantage that only liquids need to be reacted with one another, which provides for easier dosing to a reactor, for example by simple pumping of the components.

Hence, the invention in embodiments also covers a process to prepare potassium-functional N,N'-di(2-hydroxybenzyl) ethylenediamine-N,N'-diacetic acid salts (HBED) or derivatives thereof comprising a first step wherein a reaction is performed between formaldehyde and ethylenediamine diacetic acid or a salt thereof to give an adduct, and a second step wherein the adduct of formaldehyde and ethylenediamine diacetic acid or a salt thereof is reacted with phenol while ensuring that the pH is between 3 and 7 and the temperature is below 60° C.; or such a process comprising a first step of preparing a mixture comprising phenol and ethylenediamine diacetic acid or a salt thereof, and a second step of reacting the EDDA and phenol in this mixture with formaldehyde at a pH of between 3 and 7 and a temperature of below 60° C.; or such a process comprising a first step of preparing a mixture comprising phenol and formaldehyde and a second step of reacting the phenol and formaldehyde in this mixture with ethylenediamine diacetic acid or a salt thereof at a pH of between 3 and 7 and a temperature of below 60° C., wherein in all the above embodiments of the process the reaction of the 3 components EDDA, phenol and formaldehyde is performed in a mixture that contains 0.2 to 1.1 molar equivalents of alkali metal ions on the basis of the molar amount of EDDA, and wherein the reaction mixture is subsequently processed by a step in which at least part of the organic compounds other than the formed HBED are removed from the reaction mixture and optionally recycled, during which step 50-100% of the alkali metal ions in the reaction mixture are potassium ions.

It may be noted that U.S. Pat. No. 4,338,460 discloses a process for preparing phenolic propylenediamine diacetic acid compounds and that in this document an acidic pH of 2 to 6 is disclosed to be suitable for the production of di-ortho hydroxybenzyl propylenediamine diacetic acid products. However, in the examples of this same document it is demonstrated that the results obtained for propylenediamine diacetic acid could not be repeated for ethylenediamine diacetic acid products. In Example 12 where ethylene equivalents were used, a ring closure was found to take place when reacting ethylenediamine N,N' diacetic acid, formaldehyde and phenol in a water/methanol solution. The process of the present invention does not work properly for propylene diamine diacetic acid. Accordingly, one must conclude that reactions of ethylenediamine acetic acid with phenolic compounds and propylene diamine acetic acids with the same phenolic compounds are so essentially different that it will not be possible to predict reaction conditions for preparing HBED on the basis of what has been found in producing phenolic propylenediamine diacetic acid compounds. Furthermore, the fact that in Example 12 of U.S. Pat. No. 4,338,460 no reaction to form HBED takes place is thought, without Applicant wishing to be bound to any theory, to be due to the fact that the reaction mixture contains no alkali metal ions, which results in the reactants being relatively insoluble in the employed solvent mixture.

The pH during the process is between 3 and 7, and preferably between 4 and 7; it was even found to be more preferable to maintain the pH at a value of at least 5 for good yield and selectivity. In the process of the present invention a pH below 3 was found to be detrimental.

Logically during the process water needs to be present as a solvent or co-solvent to be able to determine a pH. Preferably, the EDDA reactant is added as a solution in water, but water can equally well be present with the formaldehyde reactant or be added separately to the reaction mixture.

The alkali metal ions in embodiments are added to the reaction mixture by the addition of an alkali metal hydroxide or by adding the EDDA component as an ethylenediamine diacetate alkali metal salt or as an aqueous solution containing alkali metal ions in the right amount. When the process of the present invention proceeds by premixing 2 of the 3 components, followed by a step in which the $3^{rd}$ component is added, the alkali metal in principle only needs to be present in the reaction mixture when the $3^{rd}$ component is present and the reaction to give HBED begins: however, the alkali metal ions may be added to the earlier mixture as well. In most instances the pH is adjusted to a value of between 3 and 7 by the addition of an alkali metal hydroxide, more preferably in an amount of between 0.2 and 1.1 molar equivalents on the basis of the molar amount of ethylenediamine diacetic acid or—which is effectively the same—by adding the EDDA component as an ethylenediamine diacetate salt or aqueous solution containing 0.2 to 1.1 equivalents of an alkali metal countercation. More preferably, the alkali metal is present in 0.8-1.0 molar equivalent on EDDA moles, even more preferably 0.85-0.98 molar equivalent. In all the above cases it is the most efficient and thus preferred to have 50 to 100% of the alkali metal molar amount immediately be potassium. It should be noted, however, that the above equivalents are depending on the purity of the raw materials during the reaction and their effect on the pH during the process.

In an embodiment, further alkali metal is added to the reaction mixture between the step in which the EDDA, phenol and formaldehyde are reacted to HBED and the processing step (in some instances causing an increase of the pH to higher than 7); this can be potassium but also may be another alkali metal, as long as the molar amount of potassium on total alkali metal moles is in the right molar range of 50-100% during the processing step. It is also possible to perform the earlier reaction between EDDA, phenol and formaldehyde in the presence of alkali metal containing a molar percentage of potassium outside the 50-100% on the total molar amount of alkali metal and to adjust the amount of potassium within this range by adding further potassium to the reaction mixture. For example, it is possible to perform the reaction of EDDA, phenol and formaldehyde in the presence of 0.2-1.1 equivalent of sodium ions and subsequently add an amount of potassium to the reaction mixture that is at least as high on a molar amount as the amount of sodium and still be capable of processing the reaction products in line with the process of the present invention. This is beneficial if the EDDA component used in the process of the present invention is for example only present as a sodium salt on the manufacturing site.

In a preferred embodiment of the present invention the molar amount of potassium on total alkali metal moles is in the range 60 to 99%, even more preferably 70 to 98% for both the process and the products obtainable therewith.

In a preferred embodiment the process of the present invention contains a next step wherein the product obtained is converted to a derivative of the salt such as the acid, another salt or metal complex. As the product of the process initially will be an alkali metal salt of HBED wherein 50-100% of these alkali metal ions are potassium ions, converting to another salt also covers a step of adding more base, such as potassium hydroxide, and converting the HBED salt to one containing more equivalents of, potassium, countercations, or adding an acid and replacing part of the alkali metal, potassium, ions with protons. Most preferably, in a step following the processing step the prepared HBED is contacted with metal cations to form a chelate complex, wherein in even more preferred embodiments these metals are chosen from the group of iron, zinc, manganese and copper. All the above conversions are within the skills of someone skilled in the art.

In another preferred embodiment, the process contains an additional step of removing unreacted starting materials and/or by-products, a drying step, or both. This step and the above step of converting the product to an acid, salt or complex can be performed in any order.

The process of the invention comprises a processing step in which organic compounds are at least partly removed, and optionally recycled, such as an excess of phenol or formaldehyde that is used. A preferred way of at least partly removing these organic compounds is performing an extraction step with or without recycling the organic fraction back into the process. In the extraction the HBED product will for the major part be collected in the aqueous phase.

As indicated, the HBED product or derivative, such as the metal complex made from the HBED product, in some embodiments can be dried. The drying step can be performed by any drying method that a skilled person is aware of, such as drum drying, solvent evaporation, crystallization, spray drying, and in a preferred embodiment is a spray drying step.

Spray drying is preferably done in a spray drying apparatus to which the—in most instances aqueous—solution or slurry and the air are passed concurrently or countercurrently, with more preferably a temperature gradient between the aqueous solution and the incoming air in the range from 70 to 350° C., by atomizing the aqueous solution into fine liquid droplets.

The atomizing can be done by feeding an aqueous solution onto one or more disks which preferably rotate at a peripheral speed of $>=100$ m/s, or by compressing it by means of a pump to a pressure of, in one embodiment, $>=20$ bar absolute, preferably 40 to 60 bar and, at this pressure, feeding it into the drying apparatus via one or more jets. If nozzles are used, they are preferably a few mm in size, even more preferably between 2 and 3 mm.

In a preferred embodiment, the atomizing occurs with addition of seeds, such as a crystalline fine dust, in the aqueous solution. The seeds in one embodiment have an upper limit for an average particle diameter lower by at least a factor of 2 than the lower limit of an average particle diameter of the powder obtained by the spray drying process. Preferably, the fraction of the seeds is from 0.1 to 50% by weight, preferably 0.1 to 20% by weight, based on the weight of the powder obtained by the process.

Another advantage of the present invention is that when a drying step is added, such as in preferred embodiments a spray drying step, the process leads to solid materials with improved properties, like improved storage and handling properties, wherein the drying step itself also proceeds without any problems such as dusting, caking, uneven particle sizes, plugging of the spray nozzle.

In further preferred embodiments the temperature during the process is between 0 and 60° C., preferably between 20 and 50° C., even more preferably between 30 and 50° C.

In yet other preferred embodiments of the process of the present invention the molar ratio of phenol:ethylenediamine diacetic acid (or a salt thereof) is higher than 8:1, more preferably up to 20:1; most preferably it is between 10:1 and 14:1. It is also preferred to perform the reaction in phenol as a solvent, suitably in the substantial or full absence of other solvents than water. This makes it possible to avoid contamination with other compounds. The unreacted phenol can be recycled without any problems, so in a more preferred embodiment phenol is used as a (main) solvent and the process contains a step of recycling unreacted solvent.

Preferably, the molar ratio of formaldehyde:ethylenediamine diacetic acid (or a salt thereof) is between 1.8:1 and 2.2:1. More than 2.2 molar equivalents of formaldehyde will give side reactions with phenol (which is also preferably dosed in a molar excess).

In yet another preferred embodiment it is ensured that the components, most importantly the EDDA, are fully dissolved in the reaction mixture during the process, which provides for a homogeneous reaction mixture that can be easily stirred and also leads to higher yields and less side products.

The invention is illustrated by the following Examples

EXAMPLES

In all Examples where it is indicated that components are used in a certain percentage, like 95% phenol, the remaining percents are water. In addition, all solutions are aqueous solutions.

Example 1. HBED Production and Processing With 100% of Alkali Metal Ions Being Potassium 44.7 g of a 45.8% potassium hydroxide solution (0.365 mole) were added to a slurry of 66.8 g of 99% ethylenediamine-N,N'-diacetic acid (0.375 mole) in 93.6 g of water. 54.4 g of a 41.0% formaldehyde solution (0.743 mole) were added and the reaction mixture was stirred at room temperature for 30 minutes to obtain a clear solution. This solution was added in 30 minutes to 445.8 g of 95% phenol (4.50 moles) and the reaction mixture was stirred at 35° C. for 24 h, during which time the pH increased from slightly below 6 to slightly above. After 24 h, o,o-HBED was obtained in 79.4% yield according to HPLC (EN 13368-2: 2012).

The reaction mixture was alkalized by the addition of 76.1 g of water and 47.4 g of 45.8% potassium hydroxide solution (0.387 mole) The pH increased to about 9.5. Phenol was extracted from the reaction mixture with methyl isobutyl ketone (250 ml and 3 times 125 ml). Each time a fast and clear separation occurred between the aqueous ligand solution and the organic phase. The extracted aqueous ligand solution had a pH of about 10.5 and remained clear without the formation of any precipitates. The concentration of o,o-HBED in the extracted aqueous ligand solution was approximately 26% expressed as H4-o,o-HBED.

Comparative Example 1. Production of HBED and Processing of HBED With 0% of the Alkali Metal Ions Being Potassium 26.9 g of a 50.0% sodium hydroxide solution (0.336 mole) were added to a slurry of 62.3 g of 99% ethylenediamine-N,N'-diacetic acid (0.350 mole) in 131.3 g of water. 49.1 g of a 42.4% formaldehyde solution (0.693 mole) were added and the reaction mixture was stirred at room temperature for one hour to obtain a clear solution. This solution was added in one go to 444.7 g of 88.9% phenol (4.20 moles) and the container was washed with an additional 33.7 g of water. The reaction mixture was stirred at 35° C. for 24 h, during which time the pH increased from about 5 to about 6. After 6 h, the o,o-HBED concentration was 10.85%, which corresponds to 59.7% yield. After 24 h, o,o-HBED was obtained in 83.2% yield according to HPLC (EN 13368-2:2012).

The reaction mixture was alkalized by the addition of 41.1 g of water and 33.5 g 50.0% NaOH (0.419 mole). The pH increased to about 9.5. Phenol was extracted from the reaction mixture with methyl isobutyl ketone (250 ml and 3 times 125 ml). Each time a fast and clear separation occurred between the aqueous ligand solution and the organic phase. The extracted aqueous ligand solution had a pH of about 10.5 and soon a large amount of precipitate was formed, which was identified as Na2H2-o,o-HBED. The remaining concentration of o,o-HBED in solution was approximately 6.1% expressed as H4-o,o-HBED.

Increasing the pH from about 10.5 to about 12 with additional NaOH did not improve the solubility. Only after the addition of sufficient water to lower the concentration to approximately 6.2% expressed as H4-o,o-HBED was a clear solution obtained.

Comparative Example 2. Production of HBED and Processing of HBED With 30% of Alkali Metal Ions Being Potassium 9.0 g of a 50.0% sodium hydroxide solution (0.113 mole) were added to a slurry of 20.8 g of 99% ethylenediamine-N,N'-diacetic acid (0.117 mole) in 46.1 g of water. 16.4 g of a 42.4% formaldehyde solution (0.232 mole) were added and the reaction mixture was stirred at room temperature for one hour to obtain a clear solution.

This solution was added in one go to 148.6 g of 88.9% phenol (1.40 moles) and the container was washed with an additional 9.0 g of water. The reaction mixture was stirred at 35° C. for 24 h, during which time the pH increased from about 5 to about 6. After 24 h, o,o-HBED was obtained in 81.9% yield according to HPLC (EN 13368-2:2012).

The reaction mixture was alkalized by the addition of 21.2 g of 20.5% KOH (0.077 mole) and 20.7 g of 15.0% NaOH (0.078 mole). The pH increased to about 9.5. Phenol was extracted from the reaction mixture with methyl isobutyl ketone (75 ml and 3 times 50 ml). Each time a fast and clear separation occurred between the aqueous ligand solution and the organic phase. Quickly after the fourth extraction, the aqueous ligand solution turned turbid and a lot of product precipitated. 204.7 g of water were added to obtain a clear ligand solution again. The concentration of o,o-HBED was reduced to 9.6% expressed as H4-o,o-HBED by the required dilution.

Comparative Example 3. Production of HBED and Processing of HBED With 33% of Alkali Metal Ions Being Potassium 15.5 g of a 47.0% potassium hydroxide solution (0.130 mole) were added to a slurry of 23.8 g of 99% ethylenediamine-N,N'-diacetic acid (0.134 mole) in 33.4 g of water. 17.9 g of a 44.4% formaldehyde solution (0.265 mole) were added and the reaction mixture was stirred at room temperature for 30 minutes to obtain a clear solution. This solution was added in 30 minutes to 159.5 g of 95% phenol (1.61 moles) and the reaction mixture was stirred at 35° C. for 24 h, during which time the pH increased from slightly below 6 to slightly above. After 24 h, o,o-HBED was obtained in 80.4% yield according to HPLC (EN 13368-2:2012).

The reaction mixture was alkalized by the addition of 72.0 g of 14.9% sodium hydroxide solution (0.268 mole). The pH increased to about 10. Phenol was extracted from the reaction mixture with methyl isobutyl ketone (100 ml and 3 times 50 ml). Each time a fast and clear separation occurred between the aqueous ligand solution and the organic phase. The extracted aqueous ligand solution had a pH of about 12.5. Soon after the fourth extraction, the aqueous ligand solution turned turbid and a lot of product precipitated.

Example 2. Production of HBED and Processing of HBED With 50% of Alkali Metal Ions Being Potassium 15.5 g of a 47.0% potassium hydroxide solution (0.130 mole) were added to a slurry of 23.8 g of 99% ethylenediamine-N,N'-diacetic acid (0.134 mole) in 33.4 g of water. 17.9 g of a 44.4% formaldehyde solution (0.265 mole) were added and the reaction mixture was stirred at room temperature for 30 minutes to obtain a clear solution. This solution was added in 30 minutes to 159.4 g of 95% phenol (1.61 moles) and the reaction mixture was stirred at 35° C. for 24 h, during which time the pH increased from slightly below 6 to slightly above. After 24 h, o,o-HBED was obtained in 80.4% yield according to HPLC (EN 13368-2:2012).

The reaction mixture was alkalized by the addition of 18.0 g of 21.1% potassium hydroxide solution (0.068 mole) and 53.9 g of 14.9% sodium hydroxide solution (0.201 mole). The pH increased to about 10.5. Phenol was extracted from the reaction mixture with methyl isobutyl ketone (100 ml and 3 times 50 ml). Each time a fast and clear separation occurred between the aqueous ligand solution and the organic phase. The extracted aqueous ligand solution had a pH of about 12.5. After the last extraction, the aqueous ligand solution became slightly turbid, but the solution could still be handled easily. The concentration of o,o-HBED in the extracted aqueous ligand solution was approximately 23% expressed as H4-o,o-HBED.

Example 3. Production of HBED and Processing of HBED With 52% of Alkali Metal Ions Being Potassium 30.7 g of a 20.5% potassium hydroxide solution (0.112 mole) were added to a slurry of 20.8 g of 99% ethylenediamine-N,N'-diacetic acid (0.117 mole) in 22.0 g of water. 16.5 g of a 42.4% formaldehyde solution (0.233 mole) were added and the reaction mixture was stirred at room temperature for one hour to obtain a clear solution. This solution was added in one go to 148.3 g of 88.9% phenol (1.40 moles) and the container was washed with an additional 11.8 g of water. The reaction mixture was stirred at 35° C. for 24 h, during which time the pH increased from about 5.5 to about 6. After 24 h, o,o-HBED was obtained in 83.4% yield according to HPLC (EN 13368-2:2012).

The reaction mixture was alkalized by the addition of 6.8 g of 20.5% KOH (0.025 mole) and 34.0 g of 15.0% NaOH (0.128 mole). The pH increased to about 9.5. Phenol was extracted from the reaction mixture with methyl isobutyl ketone (75 ml and 3 times 50 ml). Each time a fast and clear separation occurred between the aqueous ligand solution and the organic phase. After the last extraction, the aqueous ligand solution became slightly turbid, but the solution could still be handled easily. The concentration of o,o-HBED in the extracted aqueous ligand solution was approximately 22% expressed as H4-o,o-HBED.

Example 4. Production of HBED and Processing of HBED With 58% of Alkali Metal Ions Being Potassium 9.0 g of a 50.0% sodium hydroxide solution (0.113 mole) were added to a slurry of 20.8 g of 99% ethylenediamine-N,N'-diacetic acid (0.117 mole) in 46.1 g of water. 16.4 g of a 42.4% formaldehyde solution (0.232 mole) were added and the reaction mixture was stirred at room temperature for one hour to obtain a clear solution.

This solution was added in one go to 148.6 g of 88.9% phenol (1.40 moles) and the container was washed with an additional 9.0 g of water. The reaction mixture was stirred at 35° C. for 24 h, during which time the pH increased from about 5 to about 6. After 24 h, o,o-HBED was obtained in 81.9% yield according to HPLC (EN 13368-2:2012).

The reaction mixture was alkalized by the addition of 42.3 g of 20.5% KOH (0.155 mole). The pH increased to about 9.5. Phenol was extracted from the reaction mixture with methyl isobutyl ketone (75 ml and 3 times 50 ml). Each time a fast and clear separation occurred between the aqueous ligand solution and the organic phase. The extracted aqueous ligand solution remained clear without the formation of any precipitates. The concentration of o,o-HBED in the extracted aqueous ligand solution was approximately 22% expressed as H4-o,o-HBED.

Example 5. Production of HBED and Processing of HBED With 59% of Alkali Metal Ions Being Potassium 30.7 g of a 20.5% potassium hydroxide solution (0.112 mole) were added to a slurry of 20.8 g of 99% ethylenediamine-N,N'-diacetic acid (0.117 mole) in 22.0 g of water. 16.5 g of a 42.4% formaldehyde solution (0.233 mole) were added and the reaction mixture was stirred at room temperature for one hour to obtain a clear solution. This solution was added in one go to 148.3 g of 88.9% phenol (1.40 mole) and the container was washed with an additional 11.8 g of water. The reaction mixture was stirred at 35° C. for 24 h, during which time the pH increased from about 5.5 to about 6. After 24 h, o,o-HBED was obtained in 83.4% yield according to HPLC (EN 13368-2:2012).

The reaction mixture was alkalized by the addition of 11.0 g of 20.5% KOH (0.040 mole) and 29.9 g of 15.0% NaOH (0.112 mole). The pH increased to about 9.5. Phenol was extracted from the reaction mixture with methyl isobutyl ketone (75 ml and 3 times 50 ml). Each time a fast and clear separation occurred between the aqueous ligand solution and the organic phase. The extracted aqueous ligand solution remained clear without the formation of any precipitates. The concentration of o,o-HBED in the extracted aqueous ligand solution was approximately 22% expressed as H4-o, o-HBED.

Example 6. Production of HBED and Processing of HBED With 66% of Alkali Metal Ions Being Potassium 15.5 g of a 47.0% potassium hydroxide solution (0.130 mole) were added to a slurry of 23.8 g of 99% ethylenediamine-N,N'-diacetic acid (0.134 mole) in 33.5 g of water. 17.9 g of a 44.4% formaldehyde solution (0.265 mole) were added and the reaction mixture was stirred at room temperature for 30 minutes to obtain a clear solution. This solution was added in 30 minutes to 159.2 g of 95% phenol (1.61 moles) and the reaction mixture was stirred at 35° C. for 24 h, during which time the pH increased from about 5.5 to about 6. After 24 h, o,o-HBED was obtained in 79.3% yield according to HPLC (EN 13368-2:2012).

The reaction mixture was alkalized by the addition of 35.7 g of 21.1% potassium hydroxide solution (0.134 mole) and 36.1 g of 14.9% sodium hydroxide solution (0.134 mole). The pH increased to about 10.5. Phenol was extracted from the reaction mixture with methyl isobutyl ketone (85 ml and 3 times 50 ml). Each time a fast and clear separation occurred between the aqueous ligand solution and the organic phase. The extracted aqueous ligand solution had a pH of about 12.5 and remained clear without the formation of any precipitates. The concentration of o,o-HBED in the extracted aqueous ligand solution was approximately 22% expressed as H4-o,o-HBED

Example 7. Production of HBED and Processing of HBED With 85% of Alkali Metal Ions Being Potassium 30.7 g of a 20.5% potassium hydroxide solution (0.112 mole) were added to a slurry of 20.8 g of 99% ethylenediamine-N,N'-diacetic acid (0.117 mole) in 22.0 g of water. 16.5 g of a 42.4% formaldehyde solution (0.233 mole) were added and the reaction mixture was stirred at room temperature for one hour to obtain a clear solution. This solution was added in one go to 148.3 g of 88.9% phenol (1.40 moles) and the container was washed with an additional 11.8 g of water. The reaction mixture was stirred at 35° C. for 24 h, during which time the pH increased from about 5.5 to about 6. After 24 h, o,o-HBED was obtained in 83.4% yield according to HPLC (EN 13368-2:2012).

The reaction mixture was alkalized by the addition of 11.0 g of 20.5% KOH (0.040 mole) and 6.8 g of 15.0% NaOH (0.026 mole). The pH increased to about 8.5. Phenol was extracted from the reaction mixture with methyl isobutyl ketone (75 ml and 3 times 50 ml). Each time a fast and clear separation occurred between the aqueous ligand solution and the organic phase. The extracted aqueous ligand solution remained clear without the formation of any precipitates. The concentration of o,o-HBED in the extracted aqueous ligand solution was approximately 25% expressed as H4-o, o-HBED.

Example 8. Use of HBED Products of the Invention as a Micronutrient

A solution of 19.1 g of FeCl3.6H2O (0.071 mole) in 9.6 g of water (13.8% Fe m/m) was added to 100 g of the extracted HBED ligand solution from Example 7 (25% expressed as H4-o,o-HBED, 0.064 mole o,o-HBED). The pH of the solution was carefully adjusted to pH 8 with a 20.5% KOH solution. The resulting slurry was spray dried to obtain a solid containing 6.4% Fe chelated by o,o-HBED.

With this product, a fully randomized pot trial was performed in a greenhouse. *Citrus medica* Buddha's Hand was grown in 5-kg pots filled with a calcareous soil from Spain ($pH_{(water)}$=8.8; $pH_{(0.01\ M\ CaCl2)}$=7.9). The dose rate was 5 mg Fe per pot (three replicates); no Fe was given to the control (six replicates). Compared to the control, the treated plants were significantly greener, longer, produced both more fresh and dry matter and had taken up more Fe.

The invention claimed is:

1. Process to prepare N,N'-di(2-hydroxybenzyl) ethylenediamine-N,N'-diacetic acid and salts thereof (HBED) comprising a reaction between formaldehyde, ethylenediamine diacetic acid or a salt thereof (EDDA) and phenol, wherein the reaction mixture contains 0.2 to 1.1 molar equivalents of alkali metal ions on the basis of the molar amount of EDDA and the reaction mixture is processed by a step in which at least part of the organic compounds other than the formed HBED are removed from the reaction mixture, and optionally recycled, during which step at least 50% and up to and including 100% of the alkali metal ions in the reaction mixture are potassium ions.

2. Process of claim 1, wherein the reaction between formaldehyde, EDDA and phenol is performed at a pH of between 3 and 7 and a temperature below 60° C.

3. Process of claim 2, wherein the 0.2-1.1 equivalent of alkali metal ions on molar amount of EDDA is obtained by the addition of alkali metal hydroxide or by adding the EDDA as an ethylenediamine diacetate alkali metal salt or in an aqueous solution containing alkali metal ions.

4. Process of claim 2 comprising a first step wherein a reaction is performed between formaldehyde and ethylenediamine diacetic acid or a salt thereof to give an adduct and a second step wherein the adduct of formaldehyde and ethylenediamine diacetic acid or a salt thereof is reacted with phenol while ensuring that the pH is between 3 and 7 and the temperature is below 60° C.

5. Process of claim 2 comprising a first step of preparing a mixture comprising phenol and ethylenediamine diacetic acid or a salt thereof and a second step of reacting this mixture with formaldehyde at a pH of between 3 and 7 and a temperature of below 60° C.

6. Process of claim 2 comprising a first step of preparing a mixture comprising phenol and formaldehyde and a second step of reacting this mixture with ethylenediamine diacetic acid or a salt thereof at a pH of between 3 and 7 and a temperature of below 60° C.

7. Process of claim 1, wherein in a step between the reaction between EDDA, phenol and formaldehyde and the processing step further alkali metal is added to the reaction mixture.

8. Process of claim 7, wherein the addition of further alkali metal increases the pH to a value higher than 7.

9. Process of claim 1, wherein 60 to 100 mole % of the alkali metal in the reaction mixture during the processing step are potassium.

10. Process of claim 1 containing an additional step wherein the product is converted to the acid, another salt or metal complex.

11. Process of claim 1 containing an additional drying step.

12. Process of claim 11, wherein the drying step is a spray drying step.

* * * * *